United States Patent [19]

Feinstein et al.

[11] Patent Number: 4,862,932
[45] Date of Patent: Sep. 5, 1989

[54] FRACTION COLLECTOR

[75] Inventors: Paul L. Feinstein, Berkeley; Randy Gordon-Gilmore, Benicia, both of Calif.

[73] Assignee: Bio-Rad Laboratories, Inc., Hercules, Calif.

[21] Appl. No.: 183,800

[22] Filed: Apr. 20, 1988

[51] Int. Cl.$^4$ .............................................. B65B 43/50
[52] U.S. Cl. ................................... 141/130; 141/86; 222/108; 422/64; 422/70
[58] Field of Search ............... 141/130, 86, 98, 311 A; 222/108, 109, 110, 111; 422/64, 70

[56] References Cited

U.S. PATENT DOCUMENTS

| | | | |
|---|---|---|---|
| 304,116 | 8/1884 | Menne | 222/108 |
| 352,671 | 11/1886 | Amerland | 141/86 |
| 664,991 | 1/1901 | Caswell | 222/108 |
| 692,706 | 2/1902 | Poate | 312/228 |
| 1,602,668 | 10/1926 | Hansen | 141/86 |
| 2,604,248 | 7/1952 | Gorham | 141/130 |
| 2,654,522 | 10/1953 | Gorham | 141/130 |
| 2,997,077 | 8/1961 | Rodrigues | 141/130 |
| 3,004,567 | 10/1961 | Snow et al. | 141/130 |
| 3,252,330 | 5/1966 | Kling | 141/130 |
| 3,904,372 | 9/1975 | Lightner | 141/98 |
| 3,945,412 | 3/1976 | Forsstrom | 141/130 |
| 4,171,715 | 10/1979 | Forsstrom | 141/130 |
| 4,495,975 | 1/1985 | Harstrom et al. | 141/157 |
| 4,665,758 | 5/1987 | Schaarschmidt | 141/130 |
| 4,699,767 | 10/1987 | Aihara | 141/130 |

FOREIGN PATENT DOCUMENTS 0137696 9/1979 Fed. Rep. of Germany ........ 141/86

OTHER PUBLICATIONS

ISCO Catalog 20 Apr., 1984 pp. 54-55.

Primary Examiner—Henry J. Recla
Assistant Examiner—Daniel D. Stein-Freer
Attorney, Agent, or Firm—Townsend & Townsend

[57] ABSTRACT

A fraction collector includes a base unit and a turntable rotatably mounted on the base unit for supporting a plurality of collection tubes. The upper horizontal surface of the base unit includes a receptacle which is disposed to collect fluids discharged onto the base unit. The turntable is enclosed and includes a discharge port which is aligned over the receptacle when the turntable is mounted on the base unit. In this way, fluids which are intentionally or unintentionally discharged into the turntable will be collected in the receptacle 46. Receptacle 46 also includes a discharge port which may be connected to a disposal site, typically by flexible tubing.

18 Claims, 3 Drawing Sheets

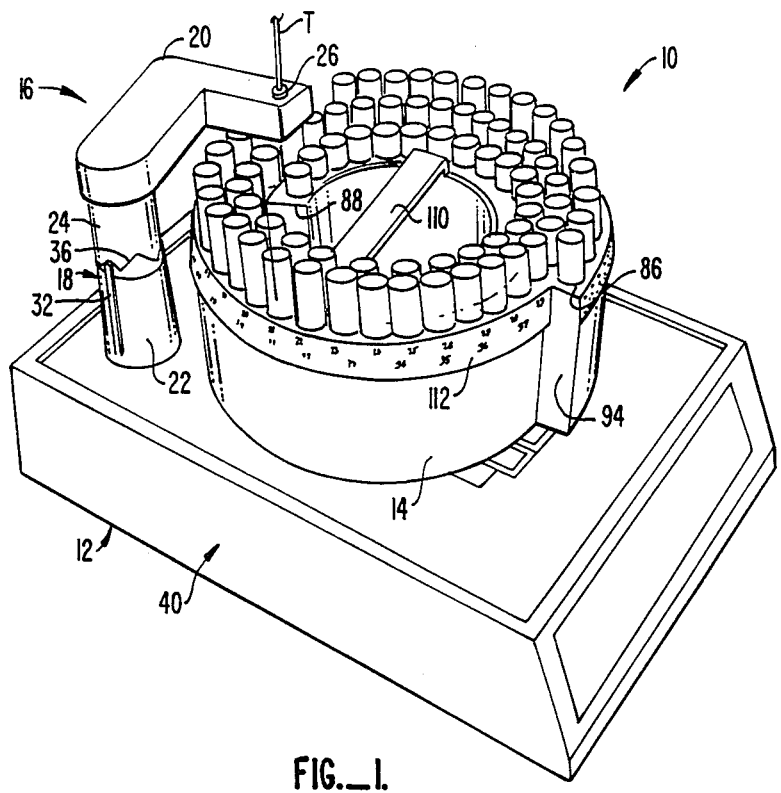
FIG._1.
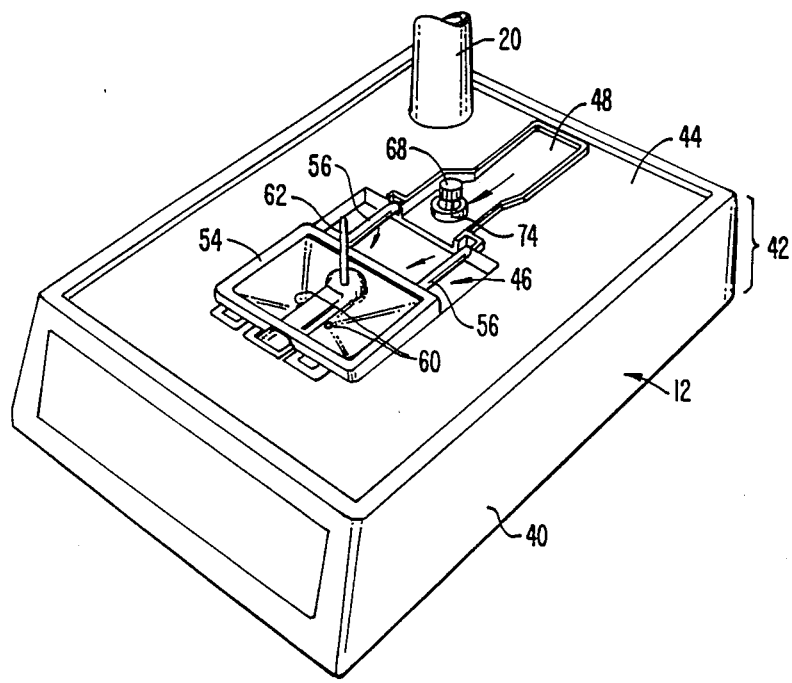
FIG._2.

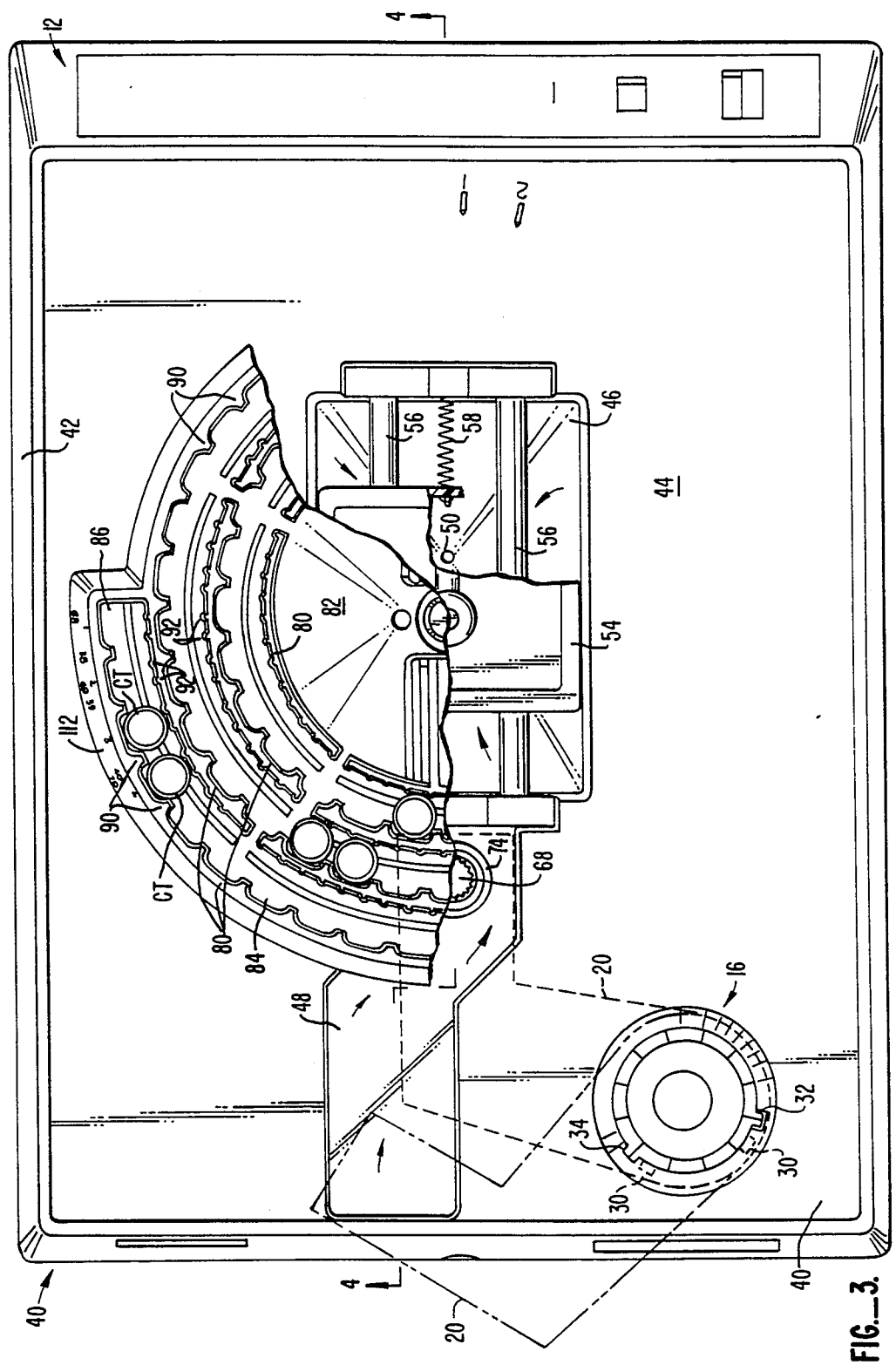
FIG._3.

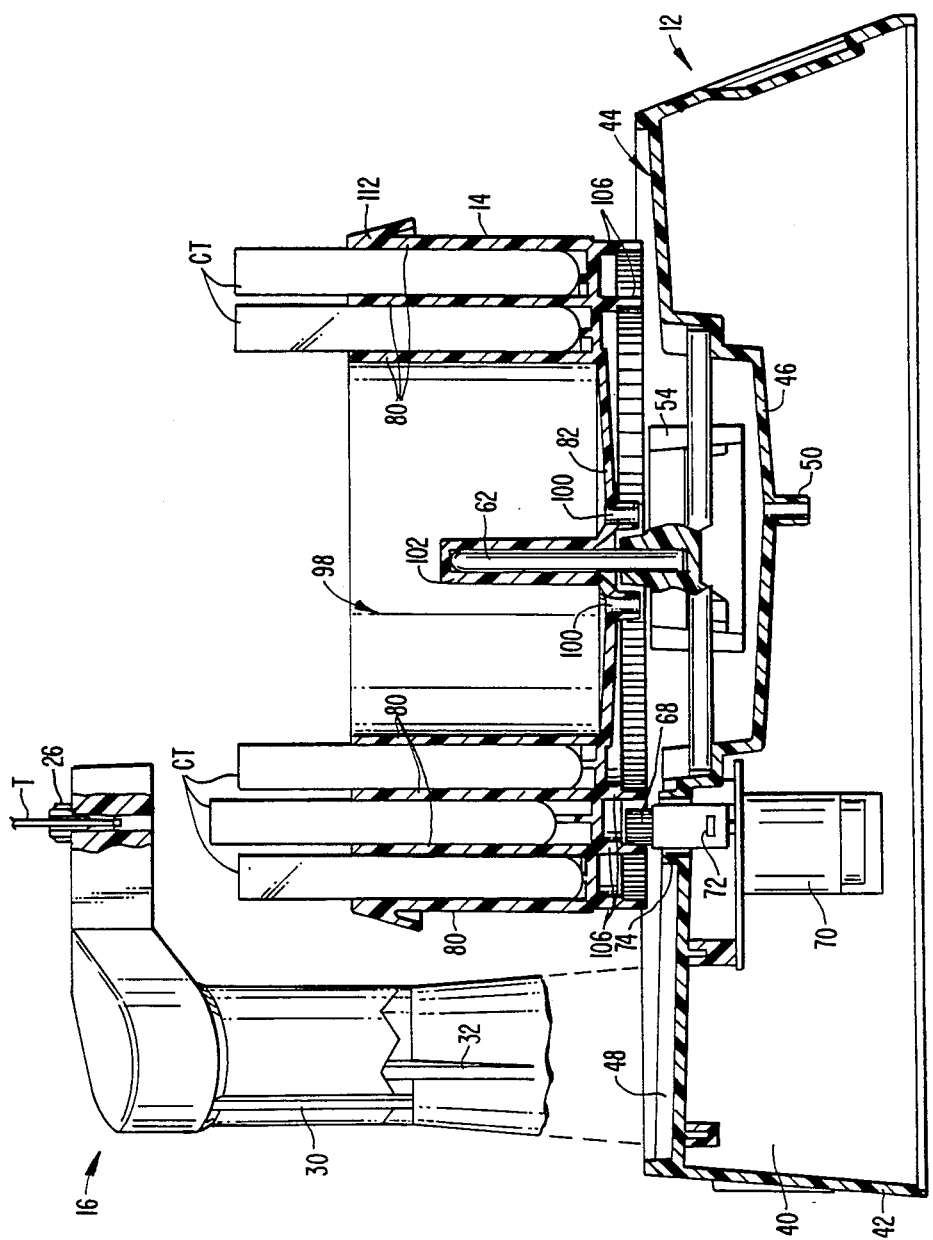
FIG._4.

FRACTION COLLECTOR

BACKGROUND OF THE INVENTION

1. Field of the Invention

The present invention relates generally to the field of liquid collection and containment, and more particularly to a system for sequentially collecting discrete liquid samples in collection tubes.

Fraction collectors are devices intended for collecting liquid samples originating from a slow flowing source, such as a chromatography column, where the composition of the liquid varies over time. Generally, fraction collectors will include a support surface capable of holding a plurality of separate collection tubes and a dispensing head capable of selectively directing the liquid sample to individual collection tubes. In this way, discrete liquid fractions of the sample may be collected in separate tubes for later analysis or use.

Fraction collectors may be broadly categorized into two groups. In the first group, the collection tubes are arranged in a generally rectangular array and the dispensing head is manipulated to selective feed the individual collection tubes. In the second group, the collection tubes are arranged in a spiral pattern and mounted on a generally circular turntable. The turntable is rotated as the dispensing head is moved radially in order to follow the spiral pattern and track the individual collection tubes. The present invention is primarily concerned with this latter group of fraction collectors.

Fraction collectors employing rotatable turntables have proved to be both reliable and economical, but also suffer from several disadvantages. First, most such fraction collectors have inadequate or no provision for disposing of waste liquid (i.e., liquid which is not desired to be collected) flowing from the dispensing head. The most common approach for handling waste streams has been to fill empty collection tubes, but that approach is an inefficient use of the fraction collector's capacity. Moreover, in the case of very large waste volumes, two or more tubes might be required to collect the entire waste. Second, in previous designs, the fraction collector turntables have usually not been enclosed. Thus, liquid which inadvertently misses the intended collection tube will be lost from the system and usually flow or splash onto the laboratory bench. The situation is not only messy, but might even be hazardous under certain circumstances. Third, the turntables in such systems are not always conveniently replaceable. While it would be frequently desirable to remove the turntable with the full complement of collection tubes in place, many systems anticipate that the collection tubes will be transferred individually to a second holding rack. Even in those systems which allow for removal and replacement of the turntable, it is frequently necessary to move the displacement head, which requires careful realignment when the system is placed back in use.

It would therefore be desirable to provide fraction collectors of the rotatable turntable-type which are capable of disposing of incoming waste streams without having to fill collection tubes which might otherwise be used for collecting desired sample fractions. It would be particularly desirable if the fraction collector could handle virtually unlimited volumes of waste, even at very high flow rates. Additionally, it would be desirable if the fraction collector allowed for convenient removal and replacement of the turntable, with a simplified mechanism for realigning the dispensing head.

2. Description of the Background Art

U.S. Pat. No. 3,004,567, describes a fraction collector comprising an open turntable capable of holding a plurality of tubes in a spiral pattern. The turntable is incrementally rotated by a gear mechanism which mates with a disc having a hole pattern corresponding to the tube pattern. The collector suffers from several drawbacks, including a lack of waste drainage capability, a drain tube support arm which must be realigned everytime the turntable is replaced, and an external drive motor and gear assembly which increases the area occupied by the device. The Cygnet ® fraction collector, available from ISCO, Inc., Lincoln, Nebr. 68505, is constructed similarly to the design disclosed in U.S. Pat. No. 3,004,567. U.S. Pat. No. 3,945,412, describes a fraction collector including an enclosed turntable capable of holding a plurality of tubes in a spiral pattern. A drop head is coupled to a cam rail on the bottom of the turntable so that the drop head can track the spirally-arranged tubes as the turntable is rotated. No provision is made for draining waste from the feed source to the turntable. U.S. Pat. No. 4,495,975, describes a fraction collector having a spiral turntable and a pivotable drop head which moves inward as the turntable is rotated. U.S. Pat. No. 4,171,715, describes a fraction collector having a spiral turntable, where the turntable is simultaneously rotated and shifted horizontally to pass tubes past a fixed drop head location.

SUMMARY OF THE INVENTION

According to the present invention, a fraction collector includes a base unit and a rotatable turntable mounted on the base unit, which turntable is capable of holding a plurality of vertical collection tubes arranged in a generally spiral pattern. The turntable is enclosed to form a collection cavity which includes a drain port near at its center of rotation. The top surface of the base unit defines a receptacle which also includes a drain port. Thus, by mounting the turntable over the base unit so that the drain port in the turntable is generally aligned with the drain port in the receptacle, fluid which is directed into the collection cavity will first drain from the turntable to the receptacle and thereafter through the drain port in the receptacle to a sink or other disposal location. In this way, virtually unlimited quantities of intentional or unintentional waste liquids can be disposed.

The turntable of the present invention is designed for easy removal and replacement. Specifically, movement of the dispensing head is limited, usually to a first position over the turntable and a second position not over the turntable. In the first position, the dispensing head is properly aligned with the turntables so that liquid will flow into a desired collection tube at all times. In the second position, the dispensing head is out of the way so that the turntable may be lifted from the base unit and replaced with a fresh turntable. The requirement of replacing the collection tubes one by one is completely eliminated.

In the preferred embodiment, the turntable is mounted on a carriage which is slidably received in the receptacle in the upper surface of the base unit. Movement of the carriage is generally limited to within the receptacle, and the carriage is spring-biased away from the dispensing head. The turntable is driven by a capstan which engages a spiral track on the bottom of the turntable, which track generally parallels the spiral tube pattern. Thus, by rotating the capstan, the turntable is rotated with individual collection tubes passing directly and sequentially beneath the dispensing head. It has been found particularly advantageous to align the drive capstan with the dispensing head, which alignment helps assure proper positioning of the collection tubes beneath the dispensing head.

DESCRIPTION OF THE DRAWINGS

FIG. 1 is a perspective view of a fraction collector constructed in accordance with the principles of the present invention.

FIG. 2 is a perspective view of the base unit of the fraction collector of FIG. 1.

FIG. 3 is a top plan view of the fraction collector of FIG. 1, with portions broken away.

FIG. 4 is a side elevational view of the fraction collector of FIG. 1, shown in cross-section.

DESCRIPTION OF THE SPECIFIC EMBODIMENTS

Referring to FIG. 1, a fraction collector 10 includes a base unit 12 and a turntable 14 rotatably mounted on the base unit. A dispensing head 16 mounted on the base unit 12 includes a vertical post 18 and an L-shaped extension arm 20. The vertical post 18 includes a fixed lower portion 22 projecting upward from the base unit 12 and a rotatable upper portion 24 which extends upward from the lower portion 22 and supports the extension arm 20 at its upper end. The extension arm 20, in turn, supports a fitting 26 (best observed in FIG. 4) which is capable of receiving and securing a flexible tube T which originates at a fluid source, such as a liquid chromatography column.

A rib 30 is formed on the upper portion 24 of the vertical post 18. Similarly, a pair of ribs 32 and 34 (FIG. 3) are formed on the lower portion 22 of the vertical post 18. Interference between the rib 30 and the pair of ribs 32 and 34 prevents rotation of the upper portion 24 outside of a desired range. The positions assumable by the upper portion 24 are further limited by a serrated interface 36 formed between the lower face of the rotatable upper portion 24 and the upper face of the fixed lower portion 22 of the vertical post 18. The spacing between the ribs 32 and 34 on the lower portion 22 of the vertical post 18 and the number and size of the serrations forming the interface 36 are selected so that the upper portion 24 of the vertical post may assume only two positions while the rib 30 is between the pair of ribs 32 and 34. A first position is then illustrated in FIGS. 1 and 4 where the fitting 26 in the dispensing head 16 is located over the turntable 14. In the second position, as illustrated in phantom in FIG. 3, the extension arm 20 of the dispensing head 16 is positioned away from the turntable 14 so that the turntable may be conveniently removed and replaced without interference from the dispensing head. It will be appreciated that once the turntable 14 is replaced, the dispensing head may conveniently be rotated back into position over the turntable and will automatically lock into alignment as a result of the serrated interface 36 and the rib stops 32 and 34 which prevent over rotation.

Referring now to FIGS. 2–4, the base unit 12 includes a shell 40, typically formed from an injection-molded plastic, such as polypropylene. The shell includes both a skirt portion 42 and a generally horizontal top portion 44. A receptacle 46 is formed as a depression in the top portion 44 of the shell 40. A trough 48 is also formed in the top surface 44 of the base unit 12. The trough 48 is formed so that it extends generally axially from one end of the base unit 12 beneath the path of the dispensing head 16 when it is moved to its position away from the turntable 14. In this way, the trough 48 will collect any liquid which is discharged from the dispensing head 16 and direct the liquid into the receptacle 46. Additionally, the top surface 44 of the base unit 12 is generally inclined downward in the direction from the periphery of the surface toward the receptacle 46. In this way, any liquid which is accidentally spilled onto the top surface 44 will tend to flow into the receptacle 46.

Receptacle 46 includes a discharge port 50 formed at its lowest point. The port 50 is formed into a nipple which can be attached to conventional flexible tubing which can be routed to a disposal location, such as a laboratory sink, or a collection vessel. In this way, liquid which is discharged from the dispensing head into the trough 48, or any other liquid which is spilled onto the upper surface 44, will eventually be collected in the receptacle 46 and flow from the receptacle through port 50. Usually, flow will be by gravity, although mechanically assisted flow may also be provided.

A carriage 54 is mounted on a pair of rods 56 which extend over the receptacle 46. A spring 58 (FIG. 3) is attached at one end to the carriage 54 and at the other end to the peripheral edge of the receptacle 46. The spring 58 urges the carriage in the rightward direction, as illustrated in FIGS. 3 and 4. The carriage 54 includes a pair of discharge ports 60 which allow fluid discharged onto the upper surface of the carriage to flow through and into the receptacle 46. The carriage 54 further includes a spindle projecting vertically upward therefrom. The spindle 62 rotatably receives the turntable thereon, as best illustrated in FIG. 4.

The base unit 12 further includes a drive capstan 68 for rotating the turntable 14, as will be described in greater detail hereinafter. The capstan 68 is driven by an electric motor 70 having an internal reducing gear, as best observed in FIG. 4. An annular dam 74 is formed about the penetration for the capstan 68 in order to prevent flow of liquid through the penetration.

Referring now in particular to FIGS. 1, 3, and 4, the turntable 14 is generally formed as a single unit, typically from injection-molded plastic, such as polypropylene. The turntable 14 includes a continuous, spiral wall 80 formed over a bottom panel 82. Together, the spiral wall 80 and bottom panel 82 define a continuous spiral channel 84 which begins at an outer end point 86 and terminates to an inner end point 88 (best observed in FIG. 1). The spiral wall 80 is formed with vertical ribs 90 and 92 formed on opposed faces of the wall, defining slots for receiving collection tubes CT in a generally vertical orientation. The dimensions and geometry of the vertical ribs 90 and 92 are, of course, not critical and it is necessary only that some provision be made for vertically supporting the collection tube at predefined locations within the spiral channel 84.

The spiral channel 84 is closed by vertical wall 94 at the outer end point 86 and is open at the inner end point 88. The bottom surface of the channel 84 is also inclined downward from a high point at the outer end point 86 to a lower point at the inner end point 88. In this way, fluid which is discharge directly into the channel 84 will flow downward through the spiral and into an open inner chamber 98 in the turntable 14. The bottom panel 82 within the open inner chamber 98 is also inclined downward toward the center where discharge ports 100 are located. Thus, any fluid which is intentionally or accidentally discharged into the spiral channel 84, or into the open inner chamber 98, will be collected within the turntable 14 and discharged through ports 100. As the ports 100 will be maintained over the upper surface of carriage 54 at all times, fluid from the turntable 14 will thus flow downward through ports 16 of the carriage 14 and into the receptacle 46.

Turntable 14 includes a bearing sleeve 102 which is mounted on the spindle 62 so that the turntable 14 is generally free to rotate relative to the carriage 54. The turntable 14 will also travel laterally with the carriage 54 as it moves along rods 56. Generally, however, both the carriage 54 and the turntable 14 are urged to the right by spring 58, absent other forces as will be described hereinafter.

A spiral cam surface 106 (FIG. 4) is formed on the lower face of bottom panel 82. The cam surface 106 is aligned with the spiral wall 86 and engages the drive capstan 68. Thus, spring 58 will generally urge the spiral cam surface 106 against the drive capsten 68 so that firm frictional engagement is maintained. Usually, the cam 68 and cam surface 106 will have mating grooves or other means to prevent slippage. Rotation of the capsten 68 by motor 70 will thus rotate the turntable selectively in either the clockwise or counterclockwise direction. As the turntable is rotated in the clockwise direction (as illustrated in FIG. 3), the spiral channel 84 moves in a direction from the outer end point 86 toward the inner end point 88. Conversely, as the turntable 14 is rotated in the counterclockwise direction, the spiral channel beneath the dispensing head 16 moves in a direction from the inner end point 88 to the outer end point 86. Thus, by incrementally rotating the drive capstan 68, individual slots within the spiral channel 84 may be brought beneath the discharge fitting 26 of the dispensing head 16. Additionally, by providing appropriate stop members proximate the outer termination point 86 and the inner termination point 88, overtravel of the turntable 14 is prevented.

When a collection tube CT is present in the receiving slot, fluid may be discharged into the collection tube. Conversely, when no collection tube CT is present in a particular slot, fluid may be discharged into the turntable 14 and will flow outward through the discharge port 50 in receptacle 46, as described previously.

Desirably, the drive capstan 68 will be vertically aligned with the discharge fitting 26 of the dispensing head 16. Such alignment helps assure that the spiral channel 84 will always be positioned directly beneath the dispensing head 16 even though the center of rotation of the turntable 14 will be moving relative to the dispensing head 16. While it would be possible to position the drive capstan 68 out of alignment with the discharge fitting 26, it would then be necessary to compensate for movement of the center of rotation of the turntable, making the collector mechanically more complicated.

In a preferred embodiment, the turntable 14 will include a handle 110 extending across the open inner chamber 98. The handle 110 allows convenient removal and replacement of the turntable onto the spindle 62 on carriage 54.

In a further preferred embodiment, the turntable of the present invention will include numbering where the collection tube CT on an inclined surface 112 formed about the upper periphery of the turntable 14. Then numbering allows convenient identification of the slots formed in the spiral channel 84.

Control of the fraction collector 10 will typically be provided by a microprocessor-based controller (not illustrated) mounted in the base unit 12. The control unit will allow rotational positioning of the turntable 14 so that a desired slot may be aligned beneath the discharge fitting 26 at dispensing head 16. Conveniently, the diameter of capstan 68 is chosen so that a fractional or integral multiple of capstan revolutions corresponds to advancement of a single slot beneath the discharge fitting 26. A flag 72 on the capstan or capstan drive can then be used to control the rotation of the turntable 14 by optically counting the number of capsten revolutions. Advancement may then be controlled by simple on/off control of the motor 70. In this way, the need to employ more expensive DC servo drives is eliminated. The use of such servo drives, however, would certainly be possible and within the scope of the present invention. Normally, an interface will be provided between the system microprocessor to allow connection of an external monitoring and control unit, such as a personal computer. In this way, operation of the fraction collector 10 can be integrated with total control of the system, typically a chromatographic analysis system.

Although the foregoing invention has been described in some detail by way of illustration and example for purposes of clarity of understanding, it will be obvious that certain changes and modifications may be practiced within the scope of the appended claims.

What is claimed is:

1. A fluid collector comprising:
    a base unit having a generally horizontal top with a receptacle formed therein, wherein the top is inclined downward toward the receptacle so that fluid spilled on the top will flow into the receptacle, said receptacle having a drain port formed therein to allow discharge of said spilled fluid;
    a dispensing arm mounted on the base unit and having a dispensing head positionable to a fixed location over the base unit;
    means for holding a plurality of collection tubes in a generally vertical orientation along a predetermined path, said means for holding being enclosed to define a cavity capable of collecting fluid directed therein and said cavity including a drain port;
    a dispensing arm mounted on the base unit and having a dispensing head positionable between a fixed location over the base unit and a second location over the horizontal top but not over the means for holding, whereby fluid spilled while the dispensing arm is at or between either location will flow into the receptacle;
    means for rotatably mounting the means for holding on the base unit so that the drain port in the cavity remains above the receptacle at all times; and
    means for rotating the means for holding relative to the base unit so that collection tubes sequentially pass beneath the dispensing head at its fixed location.

2. A fluid collector as in claim 1, wherein the predetermined path is a spiral.

3. A fluid collector comprising:
    a base unit with a generally horizontal top and having a receptacle formed in the top and a drain port formed in the receptacle;

a dispensing arm mounted on the base unit and having a dispensing head positionable to a fixed location over the base unit;

a carriage reciprocatably mounted in the receptacle in the base unit;

a receiving vessel rotatably mounted on the carriage, said vessel having an upstanding spiral wall defining a continuous spiral chamber between opposing faces of said wall, said spiral wall further including collection tube slots between the opposed faces thereof and said chamber having a drain port which discharges fluid which is directed into the chamber and not received in a collection tube;

means for simultaneously rotating the receiving vessel and shifting the carriage so that the tube slots may be incrementally advanced beneath the dispensing head.

4. A fluid collector as in claim 3, wherein the horizontal top of the base unit is inclined downward toward the receptacle so that any spilled fluid will flow to the drain.

5. A fluid collector as in claim 3, where the dispensing head is positionable between the fixed location and a second fixed location not over the means for holding.

6. A fluid collector as in claim 3, wherein the carriage is mounted on a pair of rods spanning the receptacle.

7. A fluid collector as in claim 3, wherein the drain port is located near the center of the receiving vessel and fluid must flow between the opposed faces of the spiral wall to reach said drain port.

8. A fluid collector as in claim 3, wherein the receiving vessel includes a handle.

9. A fluid collector as in claim 3, further including tube supports which elevate the collection tube over the bottom of the receiving vessel.

10. A fluid collector comprising:

a base unit with a generally horizontal top and having a receptacle formed in the top and a drain port formed in the receptacle;

a dispensing arm mounted on the base unit and having a dispensing head positionable to a fixed location over the base unit;

a carriage reciprocatably mounted in the receptacle in the base unit;

a receiving vessel rotatably mounted on the carriage, said vessel having an upstanding spiral wall defining a continuous spiral chamber between opposing faces of said wall, said spiral wall further including collection tube slots between the opposed faces thereof, a cam surface aligned with the spiral wall, and said chamber having a drain port which discharges fluid which is directed into the chamber and not received in a collection tube;

a drive gear mounted on the base unit and aligned with the dispensing head so that said gear engages the cam surface on the receiving vessel;

means for biasing the carriage so that the drive gear firmly engages the cam surface; and means for rotating the drive gear to rotationally advance the receiving vessel so that the tube slots may be advanced under the dispensing head.

11. A fluid collector as in claim 10, wherein the horizontal top of the base unit is inclined downward toward the receptacle so that any spilled fluid will flow to the drain.

12. A fluid collector as in claim 10, where the dispensing head is positionable between the fixed location and a second fixed location not over the means for holding.

13. A fluid collector as in claim 10, wherein the carriage is mounted on a pair of rods spanning the receptacle.

14. A fluid collector as in claim 10, wherein the drain port is located near the center of the receiving vessel and fluid must flow between the opposed faces of the spiral wall to reach said drain port.

15. A fluid collector as in claim 10, wherein the receiving vessel includes a handle.

16. A fluid collector as in claim 10, wherein rotation of the drive gear through a fixed angular rotation corresponds to rotational advancement of the receiving vessel from one tube slot to the next.

17. A fluid collector as in claim 16, further including means for determining the angular rotation of the drive gear in order to control advancement of the receiving vessel.

18. A fluid collector as in claim 10, wherein the means for rotating the drive includes an electric motor and reducing gear.

* * * * *